United States Patent [19]

Wasserman et al.

[11] 4,328,204

[45] May 4, 1982

[54] ABSORBABLE POLYMER-DRUG COMPOUNDS AND METHOD FOR MAKING SAME

[75] Inventors: David Wasserman, Springfield; Charles C. Versfelt, Somerville; Dowon Hahn, Flemington; Michael P. Wachter, Bloomsbury, all of N.J.

[73] Assignee: Ethicon, Inc., Somerville, N.J.

[21] Appl. No.: 773,449

[22] Filed: Mar. 2, 1977

[51] Int. Cl.³ .......................... A01N 25/26; A61J 3/00
[52] U.S. Cl. ...................................... 424/19; 424/238; 424/20; 424/21; 424/243
[58] Field of Search .................................... 424/19–22, 424/78–83, 238–243

[56] References Cited

U.S. PATENT DOCUMENTS

| | | | |
|---|---|---|---|
| 3,679,653 | 7/1972 | Schuck et al. | 260/112.5 |
| 3,755,558 | 8/1973 | Scribner | 424/243 |
| 3,773,919 | 11/1973 | Boswell et al. | 424/243 |
| 4,066,747 | 1/1978 | Capozza | 424/78 |

*Primary Examiner*—Elbert L. Roberts

[57] ABSTRACT

Drugs with active hydrogen containing groups are reacted with α-polyester homopolymers and copolymers to form compounds which slowly absorb and release the drug when implanted in animal tissue.

8 Claims, No Drawings

ABSORBABLE POLYMER-DRUG COMPOUNDS AND METHOD FOR MAKING SAME

BACKGROUND OF THE INVENTION

This invention relates to novel polymer-drug compounds and their use in providing sustained release drug delivery to human and other warm-blooded animals. The polymer-drug compounds provide a mechanism whereby the rate of release and availability of the drug may be regulated so that the quantity of a drug which is released at a particular time or at a particular site is relatively constant and uniform over extended periods of time.

Drugs are conventionally administered orally or via injection, often at a site remote from the target. Over a relatively short period of time, the drug diffuses into the circulation system of the patient and is distributed to the various organs, at least one of which is the intended target for the drug. The action of the drug on organs other than the target may result in undesirable side effects. Finally, the drug is metabolized or otherwise irreversibly removed from the organism by excretion or chemical deactivation.

When drugs are delivered orally or by injection, the level and duration of availability of the drug cannot be controlled independently; only the size and frequency of the dose can be manipulated. Typically, there is an initially high concentration of available drug at the site of injection or in the circulatory system which then decreases gradually as the drug is distributed and consumed within the body of the patient.

In controlled sustained delivery, a formulation of the drug is administered to the patient by injection or implantation. The formulation is a drug reservoir that protects the stored drug from extraneous removal mechanisms and releases the drug to the biological reservoir at a predetermined rate.

Controlled sustained delivery of a drug prevents undesirable peaking of blood levels and makes the drug available at an optimum and uniform concentration over an extended period of time. Only the released drug is subject to removal via metabolism and excretion.

U.S. Pat. Nos. 3,773,919 and 3,755,558 describe physical mixtures of various polylactides and copolymers of glycolide and lactide with some well known drugs in order to achieve a slow release of the drugs when implanted or applied topically to humans. These mixtures are intended to release the drug over an extended period of time as the polymer of the mixture is slowly absorbed in the system. However, there exists the possibility that the drugs may be extracted from the mixture by body fluids before the polymers are absorbed, leaving an unnecessary and nonfunctional mass of polymer within the organism, and making the rate of delivery of the drug unpredictable or at lease unrelated to the polymer absorption rate.

SUMMARY OF THE INVENTION

It has now been discovered that predictable release of drugs over extended periods of time can be achieved with certain drugs having active hydrogen containing groups by chemically reacting these drugs with α-polyester homopolymers and copolymers to form at least one covalent bond between the drug and polymer.

The polymer-drug compounds of the present invention are made by adding a drug having a group containing an active hydrogen atom to the polymerization reaction of the α-polyester. The drug may be added at the beginning, during, or near the end of the polymerization reaction. The drug group containing the active hydrogen atom enters into the polymerization reaction and is covalently bound to the polymer. Unreacted, unbound drug may be subsequently removed by extraction or precipitation to leave only the chemically bound drug in the polymer-drug composition.

The polymer-drug compositions are administered to the patient by injection as fluid suspensions or by implantation as solid pellets in subcutaneous or intramuscular tissue, or by topical application to affected sites.

DETAILED DESCRIPTION OF THE INVENTION

The polymer component of the sustained release polymer-drug composition may be polylactide, polyglycolide, or a copolymer of lactide and/or glycolide with up to 50% by weight of a comonomer, said comonomer having units of the formula:

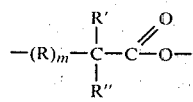

wherein
R is lower alkylene or alkylidene of up to 4 carbon atoms and is preferably methylene, ethylene or ethylidene;
m is zero or 1;
R' is H or lower alkyl of up to 3 carbon atoms and preferably is H, methyl, or ethyl;
R" is H or alkyl of up to 6 carbon atoms or phenyl or cyclohexyl when m is zero, and H or alkyl of up to 3 carbon atoms when m is 1.

It will be seen that when m is zero, R' is $CH_3$ and R" is H in the above formula, the formula describes a repeating unit derived from lactic acid. When m is zero and both R' and R" are H, the formula describes a repeating unit derived from the glycolic acid. The definition of the polymer, therefore, includes copolymers of lactide-glycolide containing any proportion of the two types of repeating units, derived from these monomers.

When R' and R" are different, the hydroxy acid from which the repeating unit is derived, and therefore the unit itself, can exist in optically active [D(+) and L(−)] forms or in optically inactive (DL- racemic) form. For example, repeating units derived from lactic acid, considered either as the principal polymer component or as the comonomer component, can be present as D(+) lactyl units, L(−) lactyl units, or DL lactyl units. A polymer containing both L(−) lactyl and DL-lactyl repeating units is defined in the present invention as a copolymer, e.g., an L(−) lactide/DL lactide copolymer.

Within the purview of the present invention, the α-polyester polymer may also be obtained from unsymmetrically substituted 1,4-dioxane-2,5-diones, as described in U.S. Pat. No. 3,960,152, incorporated herein by reference.

The polymer-drug compounds of the present invention undergo biodegradation in the body to convert the polymers into normal metabolic products, and release the drug into the system. The polymers are nonreactive toward body tissue and can be designed, by controlling molecular weight and composition, to undergo hydrolysis and thereby release the drug at a predetermined rate.

The drugs useful in the polymer-drug compositions of the present invention are those having a group containing an active hydrogen atom which can react with active sites on the α-polyester polymer chains to form a chemical bond with the polymer and terminate the polymer chain. Particularly preferred drugs are those having active —OH, —COOH or —SH groups. Other reactive groups containing active hydrogen atoms include —NH$_2$, =NH, —COSH, —CSOH, —SO$_2$H, and —SO$_3$H. Drugs containing such groups which may be used in the practice of the present invention are well known in the medical field.

Among the preferred drugs which can be reacted with the polyesters according to the present invention are contraceptive steroids designed to prevent conception in mammals. A long lasting, constant release of the drug for a period of one year or longer when implanted in females may be achieved by the use of selected polyester-drug compositions whose rate of hydrolysis provides the desired rate and duration of drug release. [Poly L(—)-lactide] polymers terminated with a hydroxyl containing drug such as ethinyl estradiol (EE), for example, hydrolyze and release the drug very slowly. Copolymers of L(—) lactide and glycolide in the 60:40 mole% range, when similarly terminated with EE, begin releasing the drug rapidly in about 25–35 days and are exhausted between 120 and 180 days when absorption of the polymer is complete. Non-crystalline copolymers of DL- lactide and glycolide in the 60:40 mole % ratios of monomer hydroyze and release the chemically bound drug even more rapidly and are exhausted more quickly. Blends or mixtures of slow and rapid hydrolyzing copolymers containing a chemically bound drug can be formulated to release drugs in a predetermined dosoage rate over extended periods of time.

Specific examples of contraceptive steroids that can be covalently bound to α-polyester polymers of the present invention include ethinyl estradiol (EE), mestranol and norethindrone.

Other estrogens besides ethinyl estradiol and mestranol, as well as gestogens other than norethindrone can also be used for terminating α-polyesters to form sustained release polymer-drug compositions. For example, male hormones such as androsterone, testosterone, and methyl testosterone have a hydroxyl group available for attachment to α-polyester polymers and copolymers, and the use of these hydroxy containing steroids as contraceptives or post-coital drugs can be made more effective and convenient by reacting the drug with an absorbable polyester, to provide a sustained and controlled release compound.

The prostaglandins may also be used to make polymer-drug compounds according to the present invention. Representative of these compounds is the PGE type prostaglandin having the formula

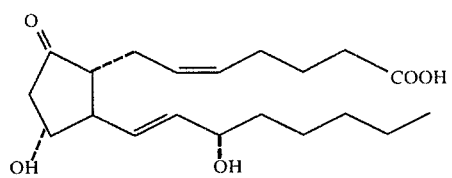

The prostaglandins are useful in stimulating smooth muscles and lowering blood pressure.

The following formulas illustrate additional drugs having a reactive hydrogen which are useful in the preparation of polymer-drug compounds according to present invention:

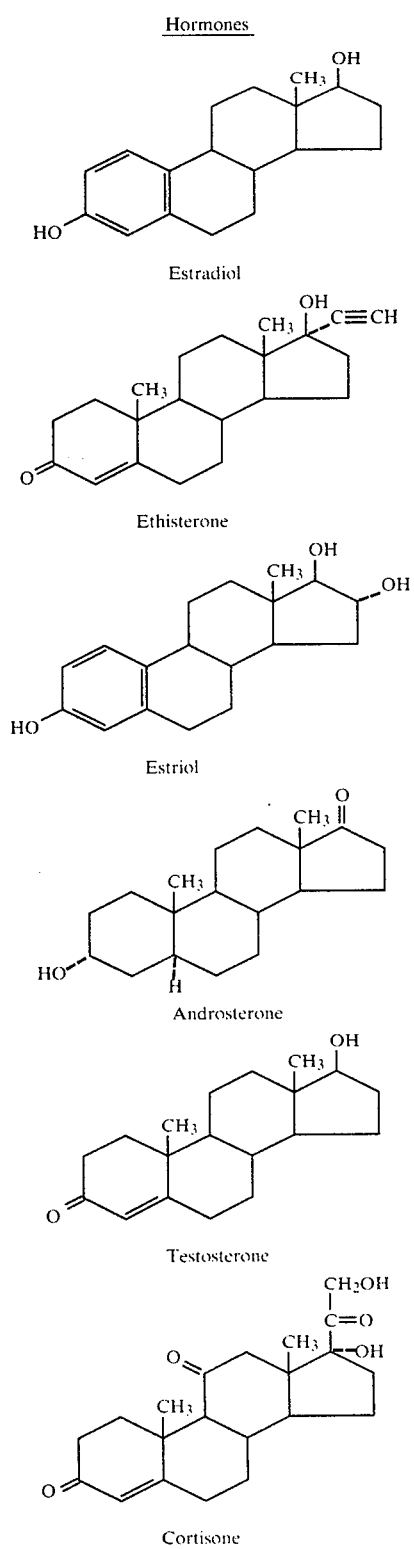

-continued
Hormones

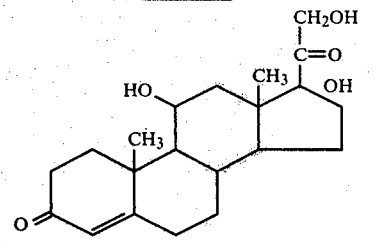

Hydrocortisone

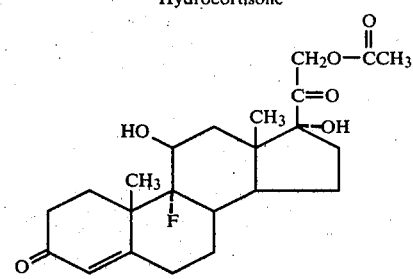

Fludrocortisone Acetate

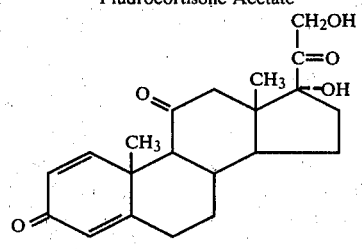

Prednisone

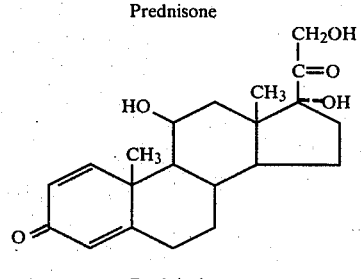

Prednisolone

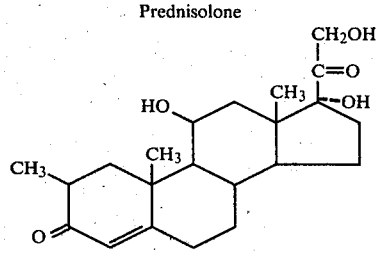

2-methyl hydrocortisone

Narcotic antagonist:

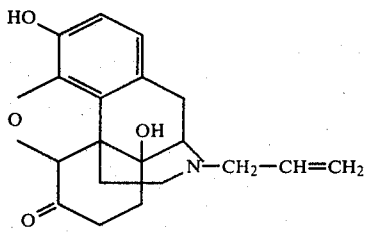

Naloxone

-continued
Hormones
Narcotic-analgesic:

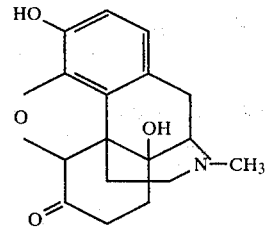

Oxymorphone

The polymer-drug compounds of the present invention can be injected as fluid suspensions, or surgically implanted as pellets of various sizes and shapes into subcutaneous cellular tissue or muscular tissue. Liquid vehicles useful for forming fluid suspensions of the polymer-drug formulation include water or aqueous solutions such as isotonic sodium chloride solution or sodium carboxymethylcellulose in water which must be made up just prior to injection due to its water sensitivity with time. Oils such as sesame oil or peanut oil containing, if desired, dissolved adjuvants such as benzyl alcohol, may also be used to prepare fluid suspensions of the polymer-drug compounds.

Alternatively, the polymer-drug compounds may be applied topically to release effective amounts of drug over a predetermined period of time. The compounds can be mixed with a suitable solvent, diluent or dispersing agent, and optionally with a propellant. When applied to living tissue by means of spraying and following removal of volatile diluent or solvent by evaporation, the polymer-drug compound forms an adherent, pharmaceutically useful, medicated film.

The relative proportions of the drug and the α-polyester reacted therewith can be varied over a wide range, depending on the results desired. The amount of drug in the compound is the amount which will be released over an extended period of time; this necessarily implies a quantity of drug greater than the conventional single dose, and the polymer-drug compound must not break down or become absorbed by the body so rapidly as to release excessive quantities of drug. While amounts of drug may range from 0.01 to 50 mole percent of compound weight, particularly valuable results have been obtained where the amount of drug ranged from about 0.1 to about 5 mole percent by weight of compound.

The preparation of polymer-drug compounds may be carried out using conventional procedures for the polymerization of α-polyester polymers as described for example in U.S. Pat. No. 3,636,956, incorporated herein by reference. In general, the polymerization comprises reacting one or more monomers in the presence of a polymerization catalyst such as stannous octoate. The polymerization is carried out under a dry, inert atmosphere at a temperature of from about 80° to 130° C., and for a time sufficient to obtain a polymer inherent viscosity of at least about 0.3 measured at 25° C. on a 0.1% solution of polymer in chloroform or hexafluoroisopropanol.

The drug may be added at any time during the polymerization reaction. Since the drug acts as a chain terminating agent, incorporation of the drug with the monomers at the beginning of the polymerization reaction predictably results in a lower molecular weight polymer with a higher concentration of bound drug. Addition of the drug later in the polymerization reaction results in a correspondingly higher molecular weight polymer with a lower concentration of bound drug. The polymerization method may accordingly be used to regulate the properties and composition of the α-polyester polymer-drug compounds of the present invention.

The present invention is further described by the following examples which are presented for purposes of illustration only and are not limiting of the invention.

EXAMPLE I

PREPARATION OF POLYMER-DRUG COMPOSITION

Twenty grams of L(−) lactide (0.139 moles) were weighed under dry nitrogen in a glove box and added to a 50 ml/long neck glass flask that had been dried in vacuo. A dry Teflon coated stir bar was aded to the flask. Five mole percent (2.1 g) of ethinyl estradiol (EE) was added, and finally 0.28 ml of a 0.33 mmole/ml solution (0.0922 mmole) of stannous octoate in dry toluene was added via a dry syringe. The flask was evacuated to remove the toluene, and when 0.1 mm Hg pressure was reached, the vacuum was released with dry nitrogen. The flask was evacuated three times and finally released with dry nitrogen to about half an atmosphere of nitrogen. The flask was sealed and heated at 105° C. with magnetic stirring until gelation of the mass. Heating was then continued for about 96° hours at 105° C. to complete the polymerization.

EXAMPLE II

The procedure of Example I was repeated using 1 mole percent of ethinyl estradiol.

EXAMPLE III

The procedure of Example I was repeated using 0.1 mole percent of ethinyl estradiol.

After cooling and degassing of the reaction mixtures in the above examples, inherent viscosity samples were taken from the bottom, middle, and edge of the polymer mass. The polymer was solidified by cooling, ground to a fine powder, extracted to remove unbound steroid, and analyzed to determine the amount of bound drug remaining in the polymer. The results are shown in Table I.

EXAMPLES IV-A to IV-H

L(−) lactide-gylcolide copolymers were terminated with ethinyl estradiol according to the method of Example I. These copolymers are absorbed in vivo much more rapidly than polylactide homopolymer of Example I and thus release the drug more quickly. The results of the analysis for bound drug in these polymers are shown in Table II.

TABLE I

| Example | Mole % EE in Sample | Grams EE in Sample | Grams L(−) lactide | Average Inherent Viscosity 0.1% (CHCl$_3$) | Mole % Bound EE |
| --- | --- | --- | --- | --- | --- |
| Control | 0 | 0 | 20.0 | 2.3 | 0 |
| I | 5.0 | 2.1 | 19.0 | 0.54 | 3.8 |
| II | 1.0 | 0.4 | 19.8 | 0.88 | 1.0 |
| III | 0.1 | 0.04 | 20.0 | 2.06 | 0.1 |

TABLE I-continued

| Example | Mole % EE in Sample | Grams EE in Sample | Grams L(−) lactide | Average Inherent Viscosity 0.1% (CHCl$_3$) | Mole % Bound EE |
| --- | --- | --- | --- | --- | --- |
| I-A* | 2.5 | 1.05 | 19.5 | — | 1.9 |

*I-A - A 50/50 mixture of Example I and the Control polymer.

TABLE II

| Example | Mole Ratio lactide/ glycolide | Mole Ratio Monomer/ catalyst | Inherent Viscosity 0.1% (HFIP) | Mole % EE Used | Mole % EE Bound |
| --- | --- | --- | --- | --- | --- |
| IV-A | 60/40 | 5828 | 6.68 | 0 | 0 |
| B | 60/40 | 5828 | 1.03 | 2.5 | 1.97 |
| C | 60/40 | 1500 | 5.2 | 0 | 0 |
| D | 60/40 | 1500 | 0.84 | 2.5 | 1.73 |
| E | 40/60 | 5828 | 5.6 | 0 | 0 |
| F | 40/60 | 5828 | 0.41 | 2.5 | 1.75 |
| G | 40/60 | 1500 | 4.46 | 0 | 0 |
| H | 40/60 | 1500 | 0.48 | 2.5 | 1.86 |

HFIP = Hexafluoroisopropanol

Estrogen assays were conducted on the compounds of Examples I and II. Groups of 5 mature female rats (weight 150 g) were bilaterally ovariectomized under ether anesthesia. Fourteen days later, daily vaginal smears were obtained in order to verify complete sterilization. At least 3 consecutive diestrual smears indicated successful surgery.

Pellets of the polymer-drug compounds of Examples I (20 mg/rat) and II (100 mg/rat) were implanted subcutaneously and daily vaginal smears were obtained to determine the incidence of estrual smears (cornified vaginal cytology). Five rats were treated with control polymers containing no drug.

Animals treated with the compound of Example I exhibited vaginal cornification which persisted for at least 4.5 months. Animals treated with the compound of Example II exhibited vaginal cornification which persisted for at least 2.5 months. Animals treated with the drug free control polymer showed no estrogenic response.

Estrogen assays were also conducted on the compound of Example IV-B by implanting 40 mg/rat of test material according to the procedure followed by Examples I and II. Animals treated with the polymer-drug combination exhibited vaginal cornification after 48 hours which persisted for an average of 40 days. As before, animals treated with the drug free control polymer showed no estrogenic response.

Adult female rats were smeared daily and at the appropriate time (proestrus) were caged overnight with males of proven fertility. On the following morning the females were examined for the presence of sperm in vaginal washings. The day on which sperm were found constituted day 1 of pregnancy. Five pregnant rats received test samples (40 mg/rat) prepared according to Example IV-B by subcutaneous implantation on day 1 of pregnancy and were sacrificed on day 20 for examination of uterine contents. Control animals were treated with drug-free copolymer (Example IV-A) on day 1 of pregnancy.

None of the five test animals showed any evidence of pregnancy, whereas the five control animals were normally pregnant with an average of 15 normal features per animal.

EXAMPLES V-A to V-F

α-Polyester homopolymer and copolymer drug compositions were made according to the method of Example I using norethindrone as the terminating drug. The product analytical results are tabulated in Table III.

TABLE III

| Example | Polymer Composition | Inherent Viscosity 0.1% (HFIP) | Mole % Norethindrone Reacted | Mole % Bound Drug |
|---|---|---|---|---|
| V-A | poly [L(−) lactide] | 0.36 | 2.5 | 0.87 |
| B | poly [L(−) lactide] | 2.86 | 0 | 0 |
| C | poly [L(−) lactide-co-glycolide] 80/20 | 0.49 | 2.5 | 2.12 |
| D | poly [L(−) lactide-co-glycolide] 80/20 | 3.54 | 0 | 0 |
| E | poly [L(−) lactide-co-glycolide] 75/25 | 0.44 | 2.5 | 1.75 |
| F | poly [L(−) lactide-co-glycolide] 75/25 | 3.92 | 0 | 0 |

The efficacy of the system of the present invention is illustrated by a series of biological experiments carried out on three groups of rabbits. The results are tabulated in Table IV. A film from compound V-A of Table III was prepared and rolled in rods. A series of units were prepared having a norethindrone content of from 2.6 to 3.7 mg per unit. These units were employed as intrauterine devices (IUD) and were positioned in one horn of the uterus of each of five rabbits numbered 1 to 5. In a like manner, a placebo was made of polymer V-B and positioned in the other horn of the uterus in each rabbit.

After two weeks the rabbits numbered 1 to 5 were bred. Approximately two weeks after the mating, the rabbits were sacrificed and the ovaries of each rabbit examined for the number of ovulations. Additionally, the horns of each uterus were examined for normal implants as well as abnormal (resorbing) implants. The results of these examinations are tabulated in Table IV.

It will be noted that in the horn of the five rabbits having the drug carrying IUD, there was an average of 3.8 ovulations while on the side having the placebos, the average number of ovulations was 4.6. The average number of implantation sites on the drug side including both normal implants and resorbed implants was 1.8. On the placebo side the average number of normally developed embryos together with those embryos being resorbed was 2.0. It appears in this case that there was only a marginal difference between the drug side and the placebo side. It is postulated that the low level response is due to the fact that compound V-A is based upon a homopolymer of lactide which had a very slow hydrolysis rate and therefore a low drug release rate.

In the next group of experiments, polymers V-C and V-D of Table III were evaluated. The polymers comprised a copolymer of 80 percent lactide, 20 percent glycolide with polymer V-C containing the drug norethindrone. The polymers were prepared as films and rolled into rods for evaluation as IUDs. Polymer V-C contained 6 to 9 mg of norethindrone per rod, which was considerably higher than the drug level of polymer V-A evaluated above.

Rods of polymers V-C and V-D were placed in opposing horns of the uterus of rabbits numbered 6 to 10 according to the procedure followed for rabbits 1 to 5 described in the foregoing. The rabbits were mated about two weeks after placement of the IUDs and sacrificed two weeks after mating. The number of ovulations was determined as tabulated in Table IV. Also, the number of fertilized ova, known as implants, was determined, including those implants in the process of being resorbed, for both the drug side and the placebo side. It is readily apparent from the data tabulated that the difference between the drug side and the placebo side for polymers V-C and V-D was dramatic.

In yet a third protocol, rabbits numbered 11 to 15 had positioned in the respective horns of the uterus, either a placebo made from polymer V-F of Table III or an IUD made from the drug carrying polymer V-E in the same mode of operation as aforementioned. Polymers of V-E and V-F are lactide and glycolide in a 75:25 ratio. The bound drug in polymer V-E was 1.75 mole percent norethindrone with about 4.3 to 6 mg per IUD. Two weeks after implantation, the rabbits were mated and the mated rabbits were then sacrificed after about two weeks. The results were again determined and tabulated. The number of ovulations in the drug side average 3.6 with observed implants averaging 1.2, while in the non-drug side the ovulations averaged 4.0 and implants 2.0. When compared with the rabbits numbered 6 to 10, rabbits numbered 11 to 15 show a higher rate of implantation, but still significantly lower than that obtained with placebos.

TABLE IV

| Ex. | Rabbits | Total Days IUD in Place | Uterine Horn With Drug-Containing IUD | | | Uterine Horn With Placebo IUD | | |
|---|---|---|---|---|---|---|---|---|
| | | | Number of Ovulation Sites | Normal Implants | Resorbing Implants | Number of Ovulation Sites | Normal Implants | Resorbing Implants |
| V-A | 1 | 28 | 4 | 2 | 0 | 4 | 2 | 0 |
| | 2 | 27 | 3 | 1 | 0 | 4 | 2 | 0 |
| | 3 | 27 | 4 | 2 | 1 | 3 | 1 | 1 |
| | 4 | 27 | 3 | 2 | 1 | 6 | 4 | 0 |
| | 5 | 30 | 5 | 0 | 0 | 6 | 0 | 0 |
| | Average | | 3.8 | 1.4 | 0.4 | 4.6 | 1.8 | 0.2 |
| V-C | 6 | 26 | 3 | 2 | 0 | 5 | 4 | 0 |
| | 7 | 27 | 1 | 1 | 0 | 5 | 3 | 1 |
| | 8 | 27 | 1 | 0 | 0 | 7 | 6 | 0 |
| | 9 | 27 | 2 | 1 | 0 | 7 | 2 | 0 |
| | 10 | 30 | 3 | 0 | 0 | 4 | 0 | 0 |
| | Average | | 2.0 | 0.8 | 0 | 5.6 | 3.0 | 0.2 |
| V-E | 11 | 30 | 1 | 0 | 0 | 6 | 0 | 0 |

TABLE IV-continued

| | | | Uterine Horn With Drug-Containing IUD | | | Uterine Horn With Placebo IUD | | |
|---|---|---|---|---|---|---|---|---|
| Ex. | Rabbits | Total Days IUD in Place | Number of Ovulation Sites | Normal Implants | Resorbing Implants | Number of Ovulation Sites | Normal Implants | Resorbing Implants |
| | 12 | 30 | 6 | 1 | 0 | 3 | 2 | 1 |
| | 13 | 30 | 1 | 1 | 0 | 4 | 3 | 0 |
| | 14 | 30 | 3 | 2 | 1 | 6 | 4 | 0 |
| | 15 | 30 | 7 | 1 | 0 | 1 | 0 | 0 |
| | | Average | 3.6 | 1.0 | 0.2 | 4.0 | 1.8 | 0.2 |

The following discussion is presented with regard to some of the polymers evaluated in the preceding Examples to provide further elucidative teachings with regard to purifying polymer-drug compounds, and casting films thereof. Essentially, the polymers considered may be categorized as polylactide homopolymers and copolymers of lactide and glycolide containing ethinyl estradiol or norethindrone.

It will be appreciated that it is often desirable to remove any unbound drug as well as unreacted monomer that may be present in the polymer-drug compound. In regard to the ethinyl estradiol/polylactide homopolymers of Examples I, II and III, the purification was accomplished via Soxhlet extraction in methyl alcohol. These three examples were analyzed after extraction for bound ethinyl estradiol (EE) by TLC spectrodensitometry to obtain the values shown in the last column of Table I. Example I posed certain additional problems in casting films and required a further step of purification by recrystallization. The recrystallized polymer-drug compound was diluted 50% with control polylactide and cast to obtain a film containing 1.9 mole % of bound drug.

The 60/40 lactide/glycolide copolymers with ethinyl estradiol of Examples IV-A to IV-D above were generally not receptive to single extraction to remove the unbound drug. Attempted Soxhlet extraction caused the polymer to degrade, and extraction without heat by means of conventional solvents was not effective. It was discovered that purification could be achieved by recrystallization from a mixture of chloroform and heptane. Films were then cast from chloroform, and the bound ethinyl estradiol was determined to be 1.97 mole % as shown for Example IV-B in Table II.

In Examples IV-F and IV-H, the ratio of the lactide/glycolide copolymer was reversed to 40/60. Again, simple extraction with various solvents did not produce useful results, and Soxhlet extraction with methyl alcohol proved to be unsatisfactory. However, purification was achieved by Soxhlet extraction in carbon tetrachloride (288 hours) followed by final treatment with chloroform, and useful solid polymers were obtained.

It was found that problems were also encountered in the purification of polylactide polymer and lactide/glycolide copolymers containing norethindrone. In those instances, Soxhlet extraction was unsuccessful and purification was achieved by recrystallization. Example V-A, for example, was recrystallized from a 30/70 mixture of chloroform and heptane. The resulting white polymer was washed repeatedly with hexane followed by drying under vacuum. A solvent comprising a 70/30 mixture of cyclohexane and ethyl acetate is also useful in the recrystallization of this polymer. The amount of norethindrone in the polymer was determined by TLC spectrodensitometry using fluorescent quenching at 250 nm.

The purified polymer was dissolved in chloroform, but attempts at casting films were unsuccessful. To 2.9 g of the foregoing polymer was added 2.9 g of control polylactide polymer and the combined solids were dissolved in chloroform with some heating, poured into a plate, and the chloroform allowed to evaporate. The resulting opaque film contained 0.87 mole % bound norethindrone as reported in Table III for Example V-A.

While in most instances it will be preferable to remove unbound drug from the polymer in order that the amount and rate of drug release may be more precisely controlled, in certain circumstances it may be desirable to leave unbound drug in the polymer-drug composition. The presence of unbound drug generally results in faster initiation of drug release and high initial release dosage as the unbound drug is leached from the polymer. Subsequently, hydrolysis of the polymer with the accompanying drug release provides continued and sustained treatment after the unbound drug has been substantially leached from the composition.

We claim:

1. A method for making an α-polyester polymer-drug compound where an α-polyester polymer is end capped with a steroid drug which comprises polymerizing a monomer selected from the group consisting of lactide, glycolide, and mixtures of lactide and/or glycolide with up to 50 percent by weight of a comonomer having units of the formula:

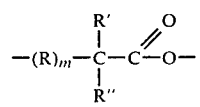

wherein
R is a lower alkylene or alkylidene of up to 4 carbon atoms;
m is zero or 1;
R' is H or a lower alkyl of up to 3 carbon atoms;
R" is selected from the group consisting of H and alkyl groups of up to 6 carbon atoms, cyclohexyl, and phenyl when m is 0, and the group consisting of H and alkyl of up to 3 carbon atoms when m is 1, with a steroid drug having a group containing an active hydrogen atom, said polymerization being conducted under a dry inert atmosphere in the presence of a polymerization catalyst and at a temperature of from 80° to 130° C. for a time sufficient to obtain a polymerization product having an inherent viscosity of at least 0.3 at 0.1% concentration in chloroform or hexafluoroisopropanol at 25° C., and thereafter cooling said polymerization product to obtain a solid polymer-drug product.

2. The method of claim 1 wherein the drug comprises from 0.01 to 50 mole percent by weight of the total weight of monomer plus drug.

3. The method of claim 1 wherein the drug is a contraceptive steroid.

4. The method of claim 3 wherein the drug is selected from the group consisting of ethinyl estradiol and norethindrone.

5. The method of claim 1 wherein the α-polyester polymer-drug compound is extracted with a solvent for said monomers and drugs to remove unreacted monomers and drugs from said polymer-drug compound.

6. A method of claim 5 wherein said monomers are lactide and glycolide, said drug is ethinyl estradiol, and said solvent is methyl alcohol.

7. A method of claim 1 wherein the α-polyester polymer-drug compound is recrystallized from a solvent for said compound to remove unreacted monomers and drug from said compound.

8. A method of claim 7 wherein said solvent is selected from the group consisting of mixtures of chloroform and hexane, mixtures of chloroform and heptane, and mixtures of cyclohexane and ethyl acetate.

* * * * *